United States Patent
An et al.

(10) Patent No.: US 10,506,987 B2
(45) Date of Patent: Dec. 17, 2019

(54) READMISSION RISK ASSESSMENT BASED ON CHRONOBIOLOGICAL RHYTHMS

(71) Applicant: Cardiac Pacemakers, Inc., St. Paul, MN (US)

(72) Inventors: Qi An, Blaine, MN (US); Viktoria A. Averina, Shoreview, MN (US); Julie A. Thompson, Circle Pines, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 330 days.

(21) Appl. No.: 15/633,278

(22) Filed: Jun. 26, 2017

(65) Prior Publication Data

US 2018/0008204 A1 Jan. 11, 2018

Related U.S. Application Data

(60) Provisional application No. 62/358,974, filed on Jul. 6, 2016.

(51) Int. Cl.
| | |
|---|---|
| *A61B 5/00* | (2006.01) |
| *A61B 5/0205* | (2006.01) |
| *G16H 50/30* | (2018.01) |
| *G16H 40/20* | (2018.01) |
| *G16H 20/10* | (2018.01) |
| *A61B 5/11* | (2006.01) |
| *A61B 5/08* | (2006.01) |
| *A61B 7/04* | (2006.01) |
| *A61B 5/024* | (2006.01) |

(Continued)

(52) U.S. Cl.
CPC .......... *A61B 5/7275* (2013.01); *A61B 5/0205* (2013.01); *A61B 5/4836* (2013.01); *G16H 20/10* (2018.01); *G16H 40/20* (2018.01); *G16H 50/30* (2018.01); *A61B 5/021* (2013.01); *A61B 5/024* (2013.01); *A61B 5/0538* (2013.01); *A61B 5/0816* (2013.01); *A61B 5/1116* (2013.01); *A61B 5/1118* (2013.01); *A61B 5/14546* (2013.01); *A61B 7/04* (2013.01); *G16H 20/30* (2018.01)

(58) Field of Classification Search
CPC combination set(s) only.
See application file for complete search history.

(56) References Cited

U.S. PATENT DOCUMENTS

| | | |
|---|---|---|
| 6,245,021 B1 | 6/2001 | Stampfer |
| 7,809,441 B2 | 10/2010 | Kane et al. |

(Continued)

*Primary Examiner* — Scott Luan
(74) *Attorney, Agent, or Firm* — Schwegman Lundberg & Woessner, P.A.

(57) ABSTRACT

Systems and methods for monitoring patients with a chronic disease are described. A patient management system may sense physiological signals from a patient using one or more implantable or other ambulatory sensors, and generate from the physiological signals a chronobiological rhythm indicator (CRI) such as indicating a circadian rhythm. A reference CRI associated with a prior hospital admission event of the patient may be provided to the patient management system, which compares the CRI to the reference CRI and generates a readmission risk score indicating the patient's risk of subsequent hospital readmission due to a worsened condition of the chronic disease. The readmission risk score may be provided to a user or a process, or used to initiate or adjust a therapy delivered to the patient.

20 Claims, 5 Drawing Sheets

(51) Int. Cl.
    *A61B 5/021*     (2006.01)
    *A61B 5/145*     (2006.01)
    *A61B 5/053*     (2006.01)
    *G16H 20/30*     (2018.01)

(56) References Cited

U.S. PATENT DOCUMENTS

| | | |
|---|---|---|
| 8,805,493 B2 | 8/2014 | Zhang et al. |
| 8,858,448 B2 | 10/2014 | Thakur et al. |

US 10,506,987 B2

READMISSION RISK ASSESSMENT BASED ON CHRONOBIOLOGICAL RHYTHMS

CLAIM OF PRIORITY

This application claims the benefit of priority under 35 U.S.C. § 119(e) of U.S. Provisional Patent Application Ser. No. 62/358,974, filed on Jul. 6, 2016, which is herein incorporated by reference in its entirety.

TECHNICAL FIELD

This document relates generally to medical devices, and more particularly, to systems and methods for monitoring patients having medical device.

BACKGROUND

Hospital readmission, especially for people with chronic diseases, is a major contributor to high healthcare costs and has a huge economic impact on the healthcare system. Nearly 20 percent of Medicare patients discharged from hospitals are readmitted within 30 days for an exacerbation of the diagnosed condition.

Congestive heart failure (CHF or HF) is a chronic cardiac disease and a leading cause of death in the United States. CHF occurs when the heart is unable to adequately supply enough blood to maintain a healthy physiological state. CHF may be treated by drug therapy, or by an implantable medical device (IMB) such as for providing cardiac electrostimulation therapies, including resynchronization therapy (CRT) to correct cardiac dyssynchrony within a ventricle or between ventricles.

Patients with worsened HF, such as decompensated heart failure, may have a high hospital readmission rate within six months following hospital discharge. Readmission is responsible for high cost of heart failure management. An unplanned readmission occurs when a patient is readmitted to a hospital within a certain period of time (e.g., 30 days) after having been discharged from the hospital for treatment of the same or related condition, such as heart failure, pneumonia, or other comorbidities.

Chronic disease management can reduce hospital readmissions and lower health care costs. For example, reduction of unplanned readmissions for HF or HF comorbidities may be achieved through reliably identifying the patients with worsened HF condition. Proper post-discharge patient monitoring may lead to reliable and robust readmission decisions, thereby reducing the readmission rate and providing timely treatment to those who require rehospitalization.

SUMMARY

This document discusses, among other things, a patient management system for monitoring patients with a chronic disease, such as CHF. The patient management system may sense physiological signals from a patient using one or more implantable or other ambulatory sensors, and generate from the physiological signals a chronobiological rhythm indicator (CRI) such as a circadian rhythm indicator. A reference CRI associated with a prior hospital admission event of the patient may be provided to the patient management system that compares the CRI to the reference CRI and generate a readmission risk score indicating the patient's risk of subsequent hospital readmission for a worsened condition of the chronic disease. The readmission risk score may be provided to a user or a process. The readmission risk score may be provided to a user or a process, or used to initiate or adjust a therapy delivered to the patient.

Example 1 is a system for managing a patient with a chronic disease. The system may comprise: a sensor circuit including sense amplifier circuits to sense one or more physiological signals; a signal processor circuit configured to generate a chronobiological rhythm indicator (CRI) from the one or more physiological signals; and a detector circuit coupled to the signal processor circuit and configured to determine a readmission risk score using the generated CRI and a reference CRI associated with a prior hospital admission event of the patient, the readmission risk score indicating a degree of risk of subsequent hospital readmission for a worsened condition of the chronic disease.

In Example 2, the subject matter of Example 1 may optionally include a therapy circuit adapted to initiate or adjust a therapy delivered to the patient in response to the readmission risk score satisfying a condition.

In Example 3, the subject matter of any one or more of Examples 1-2 may optionally include the detector circuit for detecting the chronic disease including a heart failure, and the signal processor circuit is configured to generate the CRI from the one or more physiological signals including: a heart sound signal; an endocardial acceleration signal; a heart rate signal; a thoracic impedance signal; a respiration signal; a pressure signal; a chemical signal; an activity intensity signal; or a posture signal.

In Example 4, the subject matter of any one or more of Examples 1-3 may optionally include a sensor selector circuit configured to select at least one physiological signal from the two or more physiological signals according to the reference CRI associated with the prior hospital admission event. The detector circuit may be configured to determine the readmission risk score using the generated CRI generated from the selected at least one physiological signal.

In Example 5, the subject matter of Example 4 may optionally include the sensor selector circuit configured to select the at least one physiological signal according to a change from a pre-admission CRI to a post-discharge CRI associated with the prior hospital admission event.

In Example 6, the subject matter of any one or more of Examples 1-5 may optionally include the signal processor circuit that is configured to generate the reference CRI from one or more physiological signals sensed during a post-discharge period following the prior hospital admission event; and the detector circuit is configured to determine the readmission risk score in response to a relative difference between the generated CRI and the reference CRI falling below a threshold.

In Example 7, the subject matter of any one or more of Examples 1-6 may optionally include the signal processor circuit that is configured to generate the reference CRI from one or more physiological signals sensed during a pre-admission period preceding the prior hospital admission event. The detector circuit may be configured to determine the readmission risk score in response to a relative difference between the generated CRI and the reference CRI exceeding a threshold.

In Example 8, the subject matter of any one or more of Examples 1-7 may optionally include the processor circuit that is configured to generate a first CRI from a first physiological signal and a second CRI from a different second physiological signal. The detector circuit may be configured to generate a first reference CRI from the first physiological signal during a first time period associated with the prior hospital admission event, and a second reference CRI from the second physiological signal during a second time period associated with the prior hospital admission event, and determine the readmission risk score using both a comparison between the first CRI and the first reference CRI and a comparison between the second CRI and the second reference CRI.

In Example 9, the subject matter of any one or more of Examples 1-8 may optionally include the detector circuit that is configured to determine the readmission risk score further using time elapsed from the prior hospital admission event.

In Example 10, the subject matter of any one or more of Examples 1-9 may optionally include the sensor circuit that is configured to sense at least two physiological signals. The signal processor circuit may include an ellipticity analyzer circuit configured to form a multidimensional data representation of the at least two physiological signals in a multidimensional signal space, and determine an ellipticity attribute from the multidimensional data representation; and the signal processor circuit is configured to generate the CRI using the ellipticity attribute.

In Example 11, the subject matter of Example 10 may optionally include the signal processor circuit that is configured to generate the reference CRI including a reference ellipticity attribute from a multidimensional data representation of at least two physiological signals during respective time periods associated with the prior hospital admission event. The detector circuit may be configured to determine the readmission risk score including a relative change of the ellipticity attribute from the reference ellipticity attribute.

In Example 12, the subject matter of any one or more of Examples 10-11 may optionally include the ellipticity analyzer circuit that is configured to determine the ellipticity attribute including a covariation pattern of the at least two physiological signals in the multidimensional signal space.

In Example 13, the subject matter of any one or more of Examples 10-12 may optionally include the ellipticity analyzer circuit that is configured to: compute a covariance matrix using the at least two physiological signals; determine, from the covariance matrix, two or more principal components in the multidimensional signal space or a plurality of eigenvalues associated with the two or more principal components; and determine the ellipticity attribute using the two or more principal components, a projection of the multidimensional data representation along at least one of the two or more determined principal components, or a relative measure among the plurality of eigenvalues.

In Example 14, the subject matter of Example 13 may optionally include the ellipticity analyzer circuit that is configured to: compute a reference covariance matrix using the at least two physiological signals during respective time periods associated with the prior hospital admission event; and determine two or more reference principal components from the reference covariance matrix; determine a first projection of the multidimensional data representation along at least one of the reference principal components, and a second projection of a multidimensional data representation of the at least two physiological signals associated with the prior hospital admission event along the at least one of the reference principal components; and generate the CRI from first projection and generate the reference CRI from the second projection; and wherein the detector circuit is configured to determine the readmission risk score including a relative change of the CRI from the reference CRI.

In Example 15, the subject matter of any one or more of Examples 1-14 may optionally include a trending circuit configured to generate a trend of CRI over time. The detector circuit may be configured to determine the readmission risk score further using the trend of CRI. The readmission risk score indicates a low readmission risk corresponding to an increasing trend of CRI, or indicates a high readmission risk corresponding to a decreasing trend of CRI.

Example 16 is a method for managing a patient with a chronic disease. The method comprises steps of: sensing one or more physiological signals; generating a chronobiological rhythm indicator (CRI) from the one or more physiological signals; and receiving a reference CRI associated with a prior hospital admission event of the patient; and determining a readmission risk score using the generated CRI and the reference CRI, the readmission risk score indicating a degree of risk of subsequent hospital readmission for a worsened condition of the chronic disease; and providing the readmission risk score to a user or a process.

In Example 17, the subject matter of Example 12 may optionally include adjusting or initiating a therapy, via a therapy delivery circuit, for delivery to the patient in response to the readmission risk score satisfying a condition.

In Example 18, the subject matter of any one or more of Examples 16-17 may optionally include selecting at least one physiological signal from the two or more physiological signals according to the reference CRI associated with the prior hospital admission event. The readmission risk score is determined using the CRI generated from the selected at least one physiological signal.

In Example 19, the subject matter of any one or more of Examples 16-18 may optionally include generating one or more reference CRIs from one or more physiological signals sensed during time periods including a post-discharge period following the prior hospital admission event or a pre-admission period preceding the prior hospital admission event. The readmission risk score may be determined using a comparison between the generated CRI and the one or more reference CRIs during the post-discharge period or the pre-admission period.

In Example 20, the subject matter of any one or more of Examples 16-19 may optionally include generating the CRI including generating a first CRI from a first physiological signal and a second CRI from a different second physiological signal. The step of receiving the reference CRI may include generating a first reference CRI from the first physiological signal during a first time period associated with the prior hospital admission event, and a second reference CRI from the second physiological signal during a second time period associated with the prior hospital admission event; and determining the readmission risk score includes a combination of both a comparison between the first CRI and the first reference CRI and a comparison between the second CRI and the second reference CRI.

In Example 21, the subject matter of any one or more of Examples 16-20 may optionally include generating the CRI that includes generating a multidimensional data representation of at least two physiological signals in a multidimensional signal space, and determining an ellipticity attribute from the multidimensional data representation. The step of receiving the reference CRI may include generating a reference ellipticity attribute from a multidimensional data representation of at least two physiological signals during respective time periods associated with the prior hospital admission event. The step of determining the readmission risk score may include computing a relative change of the ellipticity attribute from the reference ellipticity attribute.

In Example 22, the subject matter of Example 21 may optionally include the ellipticity attribute that includes a covariation pattern of the intensities of the at least two physiological signals in the multidimensional signal space.

In Example 23, the subject matter of any one or more of Examples 21-22 may optionally include determining the ellipticity attribute, which may include: computing a covariance matrix using the at least two physiological signals; determining, from the covariance matrix, two or more principal components or a plurality of eigenvalues associated with the two or more principal components; and determining the ellipticity attribute using the two or more principal components, a projection of the multidimensional data representation along at least one of the two or more determined principal components, or a relative measure among the plurality of eigenvalues.

The systems, devices, and methods discussed in this document may improve the medical technology of automated monitoring of patients with chronic disease, such as heart failure. The readmission risk analysis based on chronobiological rhythm indicator (CRI) as discussed in this document may enhance the performance and functionality of a medical system or an ambulatory medical device for detecting a chronic disease. In certain examples, the enhanced device functionality may include more timely and accurate detection of worsened HF condition at little to no additional cost, thereby reducing unplanned readmissions for HF or HF comorbidities. The improvement in system performance and functionality can provide reliable and robust readmission decisions, reduce the readmission rate and thus the healthcare costs associated with hospitalization, and provide timely treatment to those who require rehospitalization. The systems, devices, and methods discussed in this document also allow for more efficient device memory usage, such as by storing CRI that are clinically more relevant to readmission risk. As fewer hospital readmissions are resulted, device battery life can be extended, fewer unnecessary drugs and procedures may be scheduled, prescribed, or provided, and an overall system cost savings may be realized.

Although much of the discussion herein focuses on readmission of patients with worsened HF, this is meant only by way of example but not limitation. Systems and methods discussed in this document may also be suitable for monitoring patients who may be at risk of hospital readmission for various sorts of chronic diseases including, for example, coronary artery disease, chronic obstructive pulmonary disease, chronic kidney disease, among many others.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring patients with a chronic disease and assessing a risk of hospital readmission. A system may sense physiological signals from a patient using one or more implantable or other ambulatory sensors, and generate from the physiological signals a chronobiological rhythm indicator (CRI) such as indicating a degree of circadian rhythm. The patient management system may compare the CRI to a reference CRI associated with a prior hospital admission event of the patient, and generate a readmission risk score indicating a risk of subsequent hospital readmission due to a worsened condition of the chronic disease. The readmission risk score may be provided to a user or a process, or used to initiate or adjust a therapy delivered to the patient.

Figure 1:
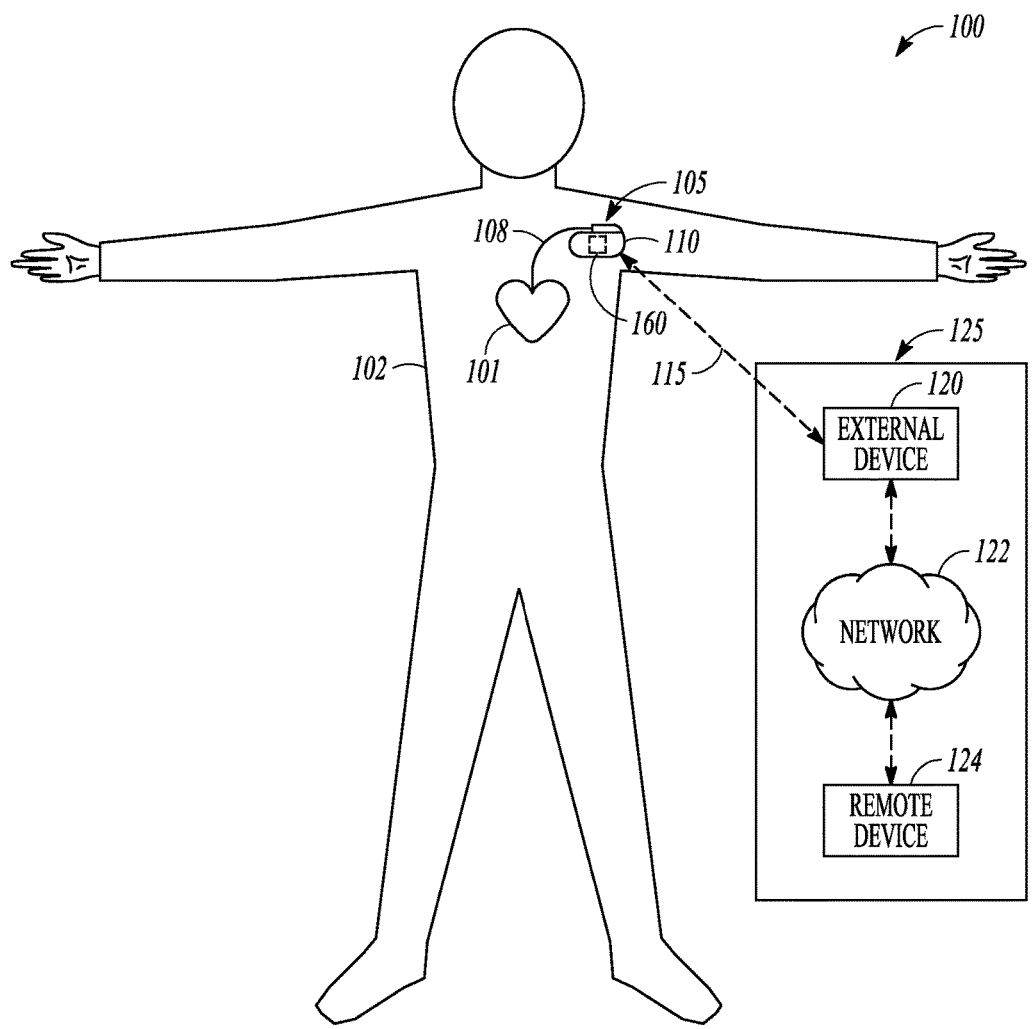
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may include an ambulatory system 105 associated with a patient body 102, an external system 125, and a telemetry link 115 providing for communication between the ambulatory system 105 and the external system 125.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may alternatively or additionally include subcutaneously implanted devices such as a subcutaneous ICD or a subcutaneous diagnostic device, wearable medical devices, or other external monitoring or therapeutic medical devices such as a bedside monitor.

The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The lead system 108 and the associated electrodes may deliver therapy to treat cardiac or pulmonary diseases. The therapies may include pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. In an example, the lead system 108 and the associated electrodes may be implanted subcutaneously or wearable on the patient body. The associated electrodes on the lead system 108 may be positioned at the patient's thorax or abdomen to sense intrinsic physiological signals indicative of cardiac or pulmonary activities, or physiological responses to diagnostic or therapeutic stimulations to a target tissue.

The AMD 110 may house an electronic circuit for sensing a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, blood chemistry such as electrolytes level, glucose level, creatinine level, blood pH level, one or more heart sounds, intracardiac acceleration, physical activity or exertion level, physiological response to activity, posture, respiration rate, tidal volume, respiratory sounds, body weight, or body temperature. The AMD 110 may initiate or adjust therapies based on the sensed physiological signals.

The AMD 100 may include a readmission risk analyzer module 160 that may detect a chronobiological rhythm from diagnostic data acquired by the ambulatory system 105. The chronobiological rhythm may include a circadian rhythm representing a daily oscillation of physical, mental and behavioral activities following an approximate 24-hour cycle. Alternatively or additionally, the chronobiological rhythm may include weekly, monthly, seasonal, or other periodic changes in physiological activities. An absence or presence, a pattern, or a change or rate of change from a reference chronobiological rhythm such as associated with an event in the patient medical history, may provide information of progression of a chronic disease or condition such as heart failure, chronic pulmonary disease, or chronic kidney disease, among others. The readmission risk analyzer module 160 may generate, based at least on the detected chronobiological rhythm, a readmission risk indicator that indicates a degree of risk of subsequent hospital readmission for a worsened chronic disease. The readmission risk analyzer module 160 may be substantially included in the AMD 110. Alternatively, the readmission risk analyzer module 160 may be substantially included in the external system 125, or be distributed between the ambulatory system 105 and the external system 125.

The external system 125 may be used to program the AMD 110. The external system 125 may include a programmer, or a patient management system that may access the ambulatory system 105 from a remote location and monitor patient status and/or adjust therapies. By way of non-limiting example, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, a capacitive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), analyzing the physiological data to generate respiratory diagnostics such as presence or worsening of a target respiratory condition, or delivering at least one therapy to treat a respiratory disease.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
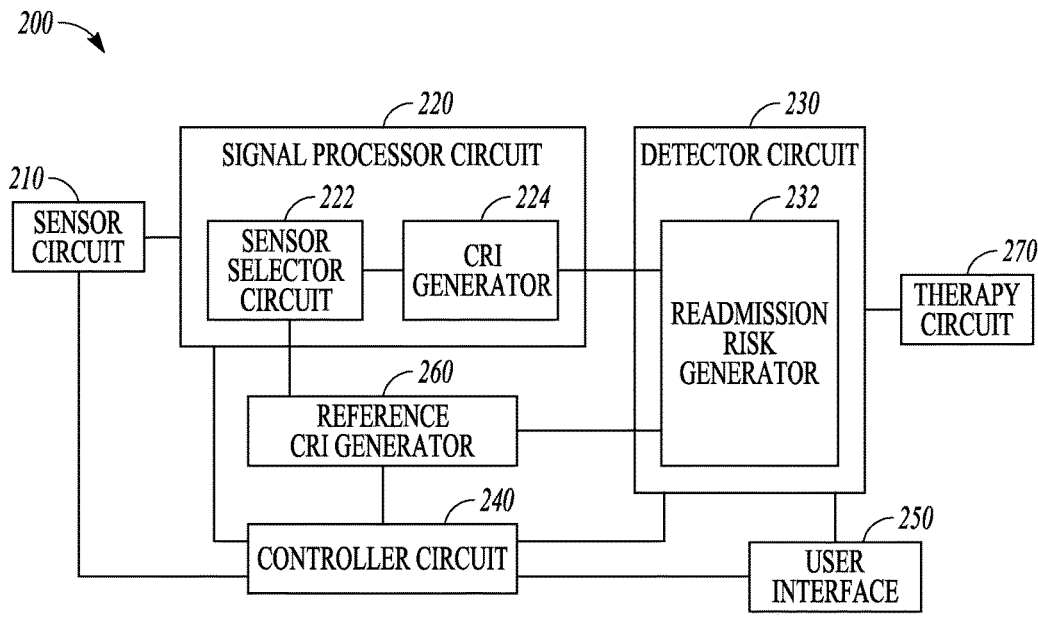
FIG. 2 illustrates generally an example of a chronic disease monitoring system for monitoring a chronic disease in a patient and determining the patient's risk of hospital readmission for the chronic disease.

FIG. 2 illustrates generally an example of a chronic disease monitoring system 200 for monitoring a chronic disease in a patient, such as a chronic heart disease (e.g., heart failure decompensation, or coronary artery disease), a chronic pulmonary disease (e.g., asthma, bronchoconstriction, COPD, pulmonary fibrosis, pneumoconiosis), or a chronic kidney disease, among others. The chronic disease monitoring system 200 may be configured to monitor a progression of the chronic disease following patient's prior discharge from the hospital, and assess a readmission risk such as due to worsening of the chronic disease.

The chronic disease monitoring system 200 may include one or more of a sensor circuit 210, a signal processor circuit 220, a detector circuit 230, a controller circuit 240, and a user interface 250. The chronic disease monitoring system 200 may include a reference chronobiological rhythm indicator (CRI) generator 260 for generating the reference CRI for use in determining a readmission risk. In some examples, the chronic disease monitoring system 200 may additionally include a therapy circuit 270 configured to deliver therapy to the patient to treat or to prevent further worsening of the chronic disease. At least a portion of the chronic disease monitoring system 200 may be implemented within the AMD 110, distributed between two or more implantable or wearable medical devices, or distributed between the AMD 110 and the external system 125.

The sensor circuit 210 may include one or more sense amplifier circuits to sense one or more physiologic signals indicative of spontaneous physiologic activities or evoked physiologic activities when a part of the patient body (such as the heart or a nerve tissue) is stimulated. The physiological sensor circuit 210 may be coupled to one or more electrodes such as on the lead system 108, or one or more implantable, wearable, holdable, or other ambulatory sensors, to sense the physiological signal(s). Examples of physiological sensors may include pressure sensors, flow sensors, impedance sensors, accelerometers, microphone sensors, respiration sensors, temperature sensors, or chemical sensors, among others. Examples of the physiological signals sensed by the physiological sensor circuit 210 may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, blood chemistry signals such as blood electrolytes level signal, glucose level signal or creatinine level signal, central venous pH value, a heart sound (HS) signal, an endocardial acceleration signal, an angular momentum sensor, a posture signal, a physical activity signal, or a respiration signal, among others. The physiological sensor circuit 210 may additionally or alternatively be coupled to a storage device that stores the physiologic information, such as an external programmer, an electronic medical record (EMR) system, or a memory unit, among other data storage devices.

The sensor circuit 210 may process the one or more physiological signals, including, for example, amplification, digitization, filtering, or other signal conditioning operations, and generate one or more signal metrics from the processed physiological signals. The one or more signal metrics may be trended over time to produce respective signal metric trends. In an example, the physiological sensor circuit 210 may receive a thoracic or cardiac impedance signal from the electrodes on the lead system 108, and generate a signal metric of impedance magnitude within a specified frequency range. In another example, the physiological sensor circuit 210 may sense a HS signal from an accelerometer, a microphone, or an acoustic sensor coupled to the AMD 110, and generate a HS metric. Examples of the HS metrics may include intensities of S1, S2, S3, or S4 heart sounds, or timing of the S1, S2, S3, or S4 heart sound with respect to a fiducial point such as a P wave, Q wave, or R wave in an ECG. In another example, the physiological sensor circuit 210 may be coupled to a respiratory sensor including one of an accelerometer, a microphone, an impedance sensor, or a flow sensor. Examples of respiration metrics may include one or more of a tidal volume, a respiration rate, a minute ventilation, a respiratory sound, or a rapid-shallow breathing index (RSBI) computed as a ratio of a respiratory rate measurement to a tidal volume measurement. In an example, the physiological sensor circuit 210 may receive multiple physiological signals from multiple sensors. For example, the physiological sensor circuit 210 may receive a pressure signal from a pressure sensor and generate two or more cardiovascular blood pressure signal metrics which may include systolic blood pressure, diastolic blood pressure, mean arterial pressure, and the timing metrics of these pressure measurements with respect to a fiducial point. The pressure sensor may alternatively or additionally sense thoracic pressure or abdominal pressure.

The signal processor circuit 220 may include a sensor selector circuit 222 and a chronobiological rhythm indicator (CRI) generator 224. The sensor selector circuit 222 may select at least one physiological signal or signal metric for use by the CRI generator 224 to generate the CRI. The selection may be based on the physiological signal or signal metric's sensitivity to the patient's chronobiological rhythms, such as an oscillatory pattern shown in a physiological signal or a signal metric trend. As illustrated in FIG. 2, the sensor selector circuit 222 may be coupled to a reference CRI generator 260 that may generate a reference indication of chronobiological rhythm associated with the patient's prior hospital admission event, or other events in the patient's medical history. The sensor selector circuit 222 may select at least one physiological signal or signal metric based on the reference indication of chronobiological rhythm. Compared to a signal or signal metric trend that manifests no or a weak chronological oscillatory pattern, a signal or signal metric trend that manifests a strong daily, weekly, monthly, or seasonal oscillatory pattern is more sensitive to the patient's chronobiological rhythm, and therefore may be selected by the sensor selector circuit 222 for generating the CRI. The strength of the oscillatory pattern may be determined using an intensity difference of the physiological signal or signal metric trend during an oscillation period, such as a maximum-to-minimum signal intensity difference during approximately 24-hour period for measuring a degree of circadian rhythm, or during other specified oscillation period. In some examples, information about physiological signals or signal metrics' sensitivities to chronobiological rhythms, including reference CRI or oscillatory patterns associated with prior hospital admission or other medical events, may be stored in a memory circuit included within the chronic disease monitoring system 200 or in a separate storage device such as the EMR system. The sensor selector circuit 222 may be communicatively coupled to the memory circuit, and select the physiological signals or signal metrics based on the oscillatory patterns of the physiological signals or signal metrics. Examples of the reference CRI generator are discussed below, such as with reference to FIG. 3.

The CRI generator 224 may generate a chronobiological rhythm indicator (CRI) from the selected physiological signals or signal metric trends. The CRI may include a statistical measure of daily, weekly, monthly, or other periodic maximum-to-minimum intensity (denoted by $X_{pp}$) difference of a physiological signal or signal metric trend X over a specified time period. In an example, the CRI includes a circadian rhythm indicator computed as a statistical measure of daily $X_{pp}$ within one day. In another example, the CRI may be computed as a statistical measure of $X_{pp}$ over a period of approximately 5-10 days. Examples of the statistical measure may include a first-order statistic such as mean, median, mode, or other central tendency measure, or a second-order statistic such as variance, standard deviation, range, inter-quartile range, or other variability or spreadness measure. The variability of the circadian rhythm may indicate a regularity of the circadian rhythm. For example, a larger variability indicates a less regular circadian rhythm, and a smaller variability indicates a more consistent and regular circadian rhythm. Additionally or alternatively, the CRI generator 224 may perform a spectral analysis of the selected physiological signals or signal metric trends, and generate a spectral peak of the chronobiological rhythm. The CRI may include one or more spectral parameters, such as a power, a center frequency, or a bandwidth of the spectral peak. In some examples, the CRI may be determined using an ellipticity attribute represented in a multidimensional signal space spanned by two or more selected physiological signals or signal metrics. Examples of the CRI based on ellipticity analysis are discussed below, such as with reference to FIGS. 5A and 5B.

Similar to the CRI generator 224, the reference CRI generator 260 may generate, for the candidate physiological signals or signal metric trends, respective reference CRI (denoted by "rCRI") over a specified time period such as associated with prior hospital admission. In an example, the rCRI may include reference statistical measure of daily maximum-to-minimum signal intensity difference (denoted by "$rX_{pp}$") over a specified time period, such as approximately 5-10 days. In another example, the rCRI may include reference spectral parameters derived from a spectral peak of the physiological signals or signal metric trends over a specified time period such as associated with prior hospital admission. In yet another example, the rCRI may include reference ellipticity attribute represented in a multidimensional signal space spanned by two or more selected physiological signals or signal metrics. In some examples, the rCRI may be predetermined and stored in a memory or other storage device included within or otherwise communicatively coupled to the chronic disease monitoring system 200.

The detector circuit 230 may include a readmission risk generator 232 coupled to the signal processor circuit 220 and the reference CRI generator 260. The readmission risk generator 232 may use the CRI and the rCRI corresponding to the selected physiological signals or signal metrics to generate a readmission risk score that indicates a degree of risk of subsequent hospital readmission due to worsening of the chronic disease. For example, if CRI generator 224 generates the CRI from the selected thoracic impedance signal, then the rCRI corresponding to the thoracic impedance signal associated with a prior hospital admission may be used in readmission risk generation. The readmission risk score may be determined as a difference, ratio, or other relative measure between the CRI and the rCRI. In an example, the readmission risk score is computed as a difference between the statistical measures of $X_{pp}$ and the statistical measure of $rX_{pp}$, or between the spectral parameter (such as the center frequency or bandwidth of the spectral peak) and the reference spectral parameter. In another example, the readmission risk score may be determined as a similarity measure between an ellipticity attribute and a reference ellipticity attribute, which is discussed below with reference to FIGS. 5A and 5B. The readmission risk score may take continuous values. Alternatively, the readmission risk score may be compared to one or more threshold values or ranges, and categorized into discrete categorical levels such as high, medium, or low risk of readmission. In some examples, the readmission risk generator 232 may generate a composite risk score using multiple physiological signals or signal metric trends, such as discussed below with reference to FIG. 4.

In an example, the detector circuit 232 may include a trending circuit for generating a trend of CRI over time. The readmission risk generator 232 may determine the readmission risk score further using the CRI trend. In an example, the readmission risk score may be inversely proportional to the CRI trend, such that an increasing trend of CRI may correspond to a low readmission risk score, and a decreasing trend of CRI may correspond to a high readmission risk.

One or more of the signal processor circuit 220 or the detector circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuit 210. Alternatively, the microprocessor circuit may be a general purpose processor that may receive and execute a set of instructions of performing the functions, methods, or techniques described herein.

The signal processor circuit 220 or the detector circuit 230 may include circuit sets comprising one or more other circuits or sub-circuits. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The controller circuit 240 may control the operations of the sensor circuit 210, the signal processor circuit 220, the detector circuit 230, the user interface 250, and the data and instruction flow between these components. The user interface 250 may include an output unit to generate a human-perceptible presentation of diagnostic information, such as a display of readmission risk score. The output unit may generate an alert if readmission risk score satisfies a specified condition, such as if the difference between the CRI and rCRI exceeds a threshold, or if the readmission risk score is categorized as a "high" risk. The output unit may also display information including the physiological signals or signal metric trends. The information may be presented in a table, a chart, a diagram, or any other types of textual, tabular, or graphical presentation formats, for displaying to a system user. The presentation of the output information may include audio or other human-perceptible media format. The output unit may provide the readmission risk score to another process such as to recommend or titrate a therapy. The user interface 250 may also include input device such as a keyboard, on-screen keyboard, mouse, trackball, touchpad, touch-screen, or other pointing or navigating devices. The input device may enable a system user such as a clinician to program the parameters used for sensing the physiological signals, generating trends of signal metrics, or generating the CRI or the rCRI for estimating readmission risk. In an example, at least a portion of the user interface 250 may be implemented in the external system 125.

In some examples, the chronic disease monitoring system 200 may additionally include a therapy circuit 270 configured to deliver a therapy to the patient. The therapy may be triggered by a command signal in response to the readmission risk score satisfying a specified condition. Examples of the therapy may include electrostimulation therapy delivered to cardiac or pulmonary tissue, heart, a nerve tissue, other target tissues in response to the detection of the target physiological event, or drug therapy including delivering drug to a tissue or organ. In some examples, therapy circuit 270 may be adjust an existing therapy based at least on the readmission risk score, such as adjusting a stimulation parameter or drug dosage.

Figure 3:
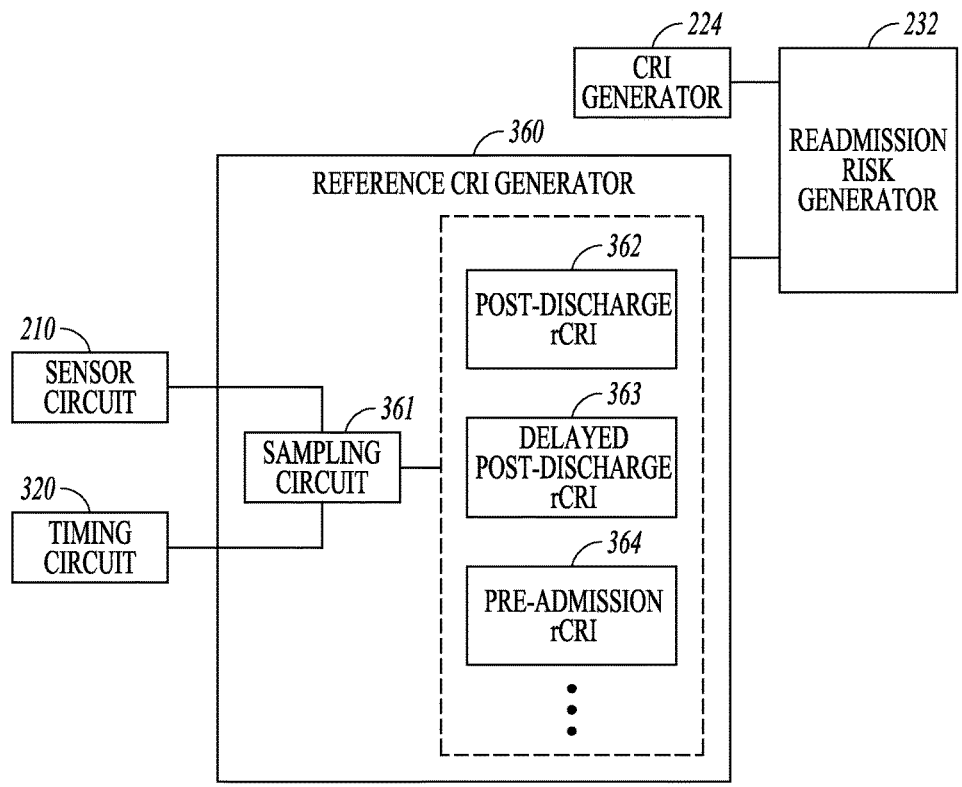
FIG. 3 illustrates generally an example of a portion of a system for generating a reference CRI from a patient's physiological signal associated with a prior medical event.

FIG. 3 illustrates generally an example of a portion of a system 300 for generating a reference CRI (rCRI) from a patient's physiological signal associated with a prior medical event. The system portion 300 may include a reference CRI generator 360, which may be an embodiment of the reference CRI generator 260 in FIG. 2. The reference CRI generator 360 may be coupled to the sensor circuit 210 for sensing a physiological signal or generating a trend of a signal metric, and a timing circuit 320 for timing different periods associated with prior hospital admission for chronic cardiac, pulmonary, or renal diseases. In an example, the timing circuit 320 may receive input from a user, such as via the user interface 250, about the beginning, end, or duration of a time period before, during, or after a prior hospital admission.

The reference CRI generator 360 may include a sampling circuit 361 that may sample the sensed physiological signal or signal metric trend during the specified time period. In an example, the sampled physiological signal or signal metric trend may include a post-discharge period following the prior hospital admission event. The post-discharge period may begin at around the hospital discharge date and last for approximately 2-5 days. In another example, a delayed post-discharge period may be used, which does not begin until after a post-discharge transition period when the patient's health status is improved and stabilized. The post-discharge transition period may be provided by a system user such as via the user interface 250. Alternatively or additionally, one or more physiological sensors may be used to detect post-discharge health status improvement and stability. The detection of the stable and improved health status may trigger the sampling circuit 361 to initiate data sampling in the delayed post-discharge period. In an example, the sampled physiological signal or signal metric trend may include a pre-admission period preceding the prior hospital admission event. The pre-admission period may have a duration of approximately 2-5 days and end just prior to hospital admission.

As previously discussed with reference to FIG. 2, the rCRI may be computed as a statistical measure of daily (or other periodic) maximum-to-minimum signal intensity difference, a spectral parameter from spectral analysis, or an ellipticity attribute in a multidimensional signal space spanned by two or more selected physiological signals or signal metrics. For a particular physiological signal or signal metric, one or more rCRI corresponding to different time periods may be generated, such as post-discharge rCRI 362, delayed post-discharge rCRI 363, or pre-admission rCRI 364 as illustrated FIG. 3. During the post-discharge period, the patient may be in recovery from a prior hospitalization for the chronic disease (such as worsening HF). During the delayed post-discharge period, the patient may be in a state of improved and stabilized health status. The post-discharge rCRI 362 and delayed post-discharge rCRI 363 therefore represent chronobiological rhythm when the patient is in an improved health status. When the readmission risk score is computed as a difference between the CRI (such as determined by the CRI generator 224) and the rCRI (such as either the post-discharge rCRI 362 or the delayed post-discharge rCRI 363), a low readmission risk score may be generated if the CRI substantially resembles the rCRI, indicating the presence of a strong chronobiological rhythm.

During the pre-admission period, the patient health status may be significantly deteriorated. The pre-admission rCRI 364 may thus correspond to worsened chronic disease state. A low readmission risk score may be generated if the CRI substantially improves from the pre-admission rCRI 364 (such as when the difference between the CRI and the pre-admission rCRI 364 exceeds a threshold value), indicating the presence of a strong chronobiological rhythm.

The readmission risk generator 232 may generate the readmission risk score using a combination of two or more of a comparison between the CRI and post-discharge CRI 362, a comparison between the CRI and the delayed post-discharge rCRI 363, and a comparison between the CRI and the pre-admission rCRI 364. The combination may include weighted sum or other linear or nonlinear combination.

The reference CRI generator 360 may generate, for each of a plurality of candidate physiological signals or signal metrics $\{X_1, X_2, \ldots, X_N\}$, respective post-discharge rCRI 362, delayed post-discharge rCRI 363, or pre-admission rCRI 364. The sensor selector circuit 222 may select a physiological signal or signal metric based on a comparison of the rCRIs, associated with a particular time period of the prior hospital admission, for all the signals or signal metrics $\{X_1, X_2, \ldots, X_N\}$. In an example, a physiological signal or signal metric $X_k$ corresponding to the largest post-discharge rCRI among $\{X_1, X_2, \ldots, X_N\}$ may be selected. Chronobiological rhythm may recover following patient discharge, resulting in an increase in post-discharge rCRI value. The signal metric $X_k$ with the largest post-discharge rCRI is more sensitive to a post-discharge recovery of chronobiological rhythm, and may therefore be preferred over a signal metric having a smaller post-discharge rCRI for assessing readmission risk. In another example, the chronobiological rhythm may diminish or become irregular just prior to hospital admission such as due to worsening of the chronic disease. A signal metric $X_k$ having a smaller corresponding pre-admission rCRI may be selected, as it may be more sensitive to pre-admission deterioration of chronobiological rhythm than a signal metric having a larger pre-admission rCRI for assessing readmission risk estimation value. In another example, the sensor selector circuit 222 may select a physiological signal or signal metric using a relative change (such as a difference) from a pre-admission rCRI to a post-discharge rCRI. Among $\{X_1, X_2, \ldots, X_N\}$, a signal metric $X_k$ with the largest change from pre-admission to post-discharge rCRI value may be more sensitive to a recovery process of chronobiological rhythm from pre-admission to post-discharge recovery period, and may therefore be selected for assessing readmission risk.

Figure 4:
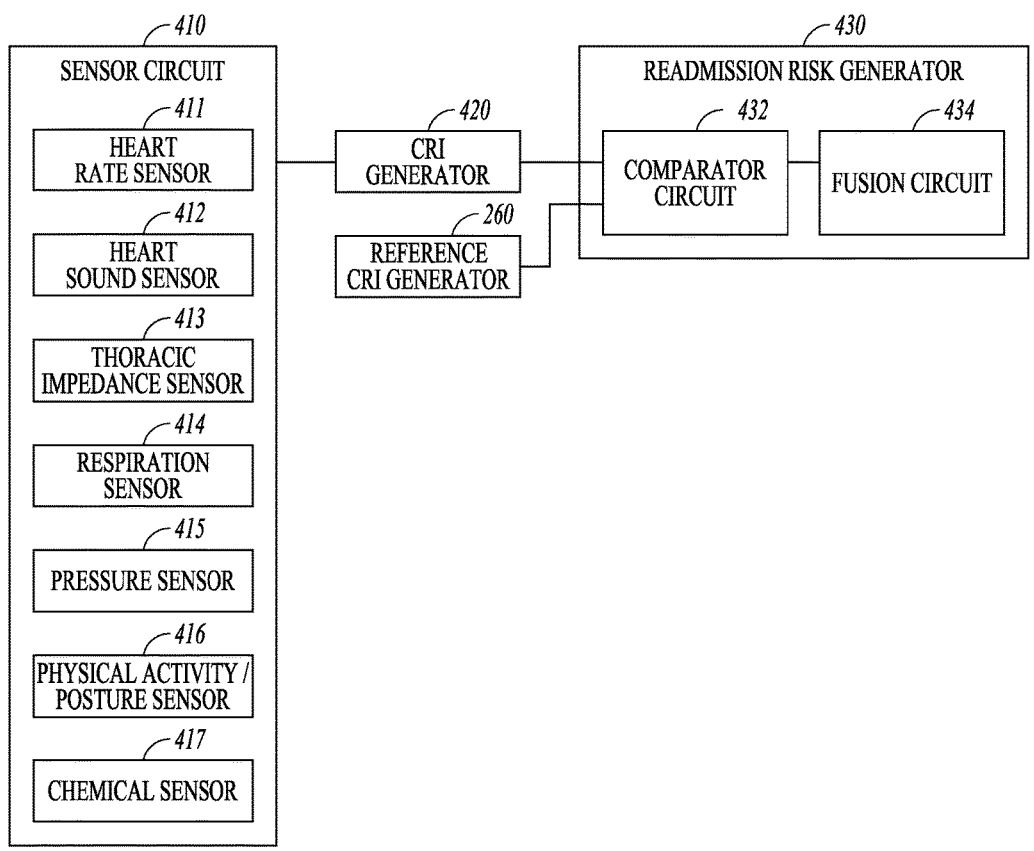
FIG. 4 illustrates generally an example of a multi-sensor readmission risk assessment system.

FIG. 4 illustrates generally an example of a multi-sensor readmission risk assessment system 400, which may be an embodiment of the chronic disease monitoring system 200. The multi-sensor readmission risk assessment system 400 may be configured to determine a patient's readmission risk based on the CRIs respectively generated from multiple sensor signals. The multi-sensor readmission risk assessment system 400 may include a sensor circuit 410 that includes a plurality of sensors configured to sense respective physiological signals from the patient. By way of non-limiting examples and as illustrated in FIG. 4, the sensors may include a heart rate sensor 411, a heart sound sensor 412, a thoracic impedance sensor 413, a respiration sensor 414, a pressure sensor 415, a physical activity/posture sensor 416, or a chemical sensor 417.

The heart rate sensor 411 may detect a heart rate (HR) signal, or a statistical measurement from the heart rate signal, such as a heart rate variability (HRV). Circadian rhythms (or oscillatory patterns at other periods) of HR or HRV, when lost, diminished, or otherwise changed from a reference level such as during a time period associated with a prior hospital admission, may indicate a change of chronic disease status, such as a worsening or improvement of HF status. For example, a healthy subject's HR manifests a daily oscillatory pattern with a lower HR during sleep than during an awake state. HRV of a healthy subject generally is lower during daytime or an awake state, and increases during nighttime or sleep. This circadian rhythms of HR or HRV may become less pronounced, more irregular, or otherwise change several hours to several days before the onset of a disease state, such as a worsening heart failure.

The HS sensor 412 may sense HS information indicative of acoustic or mechanical activity of a heart, which may include S1, S2, S3 or S4 heart sounds. Examples of the HS sensor may include an accelerometer, an acoustic sensor, a microphone, a piezo-based sensor, or other vibrational or acoustic sensors. The HS sensors may be implantable, wearable, holdable, or otherwise ambulatory sensor, and placed external to the patient or implanted inside the body. The HS sensor may be included in at least one part of an ambulatory system, such as the AMD 110, or a lead coupled to the ambulatory medical device such as for sensing endocardial acceleration. In a health subject, intensity of HS components such as S1, S2, S3, or S4 heart sounds, or cardiac timing intervals, may manifest circadian rhythm or oscillatory patterns at other periods. The intensity of HS component may be measured as peak amplitude of HS component, or signal energy within a time window for detecting a HS component. The cardiac timing intervals may include pre-ejection period or left ventricular ejection time that may be measured from a cardiac event (such as Q or R wave in an ECG signal) to a HS component (such as S1 or S2 heart sounds). This HS circadian rhythm may be lost, diminished, or otherwise changed from a reference level such as at a time period during a prior hospital admission, a change of HF status is indicated.

The thoracic impedance sensor 413 may sense thoracic impedance such as by using one or more implanted electrodes on the lead system 108 and the can housing of the AMD 110. The thoracic impedance may reflect thoracic fluid status. In a healthy subject, distribution of thoracic fluid may follow a circadian rhythm. Accordingly, the thoracic impedance may also manifest an oscillatory pattern in which the impedance is lower during night or sleep at least due to more thoracic fluid accumulation, and higher during daytime or upright position at least due to less thoracic fluid accumulation. This circadian rhythm of thoracic impedance, however, may begin to shift, become less pronounced, or otherwise change several hours to several days before the onset of a disease state, such as a worsening heart failure.

The respiration sensor 414 may include an implantable, wearable, holdable, or otherwise ambulatory sensor for sensing a respiration signal. Examples of the respiration sensor may include an accelerometer, a microphone, an impedance sensor, or a flow sensor. The respiratory sensor 414 may detect one or more respiration parameters such as one or more of a tidal volume (TV), a respiration rate (RR), a respiration rate variability (RRV), a minute ventilation (MV), or a rapid-shallow breathing index (RSBI) computed as a ratio of a respiratory rate measurement to a tidal volume measurement, among others. In a healthy subject, respiration parameters such as RR, RRV, MV, or RSBI may manifest a pronounced, regular circadian rhythm or oscillatory pattern at other periods. This circadian rhythm of respiration parameters, however, may become lost, diminish, or otherwise change from several hours to several days before the onset of a disease state, such as a worsening heart failure. The loss of diminish of the circadian rhythm of the respiration parameters may include a decrease in low-frequency component of the RR (as the subject is less likely to be active), and an increase in high-frequency component of the RR.

The pressure sensor 415 may include an implantable, wearable, holdable, or otherwise ambulatory sensor for sensing a cardiovascular blood pressure or a pressure within a heart chamber or a surround vascular structure. In healthy subjects, cardiovascular pressure follows a circadian rhythm. For instance, the blood pressure typically rises in the morning and stays elevated until late afternoon, at which time it drops off and hits its lowest point during the night. This circadian rhythm of cardiovascular pressure, however, may become less pronounced or otherwise change several hours to several days before the onset of a disease state, such as a worsening heart failure. Monitoring the circadian rhythm of cardiovascular pressure in such instances provides a tool to predict, monitor, or treat an occurrence of impending heart failure.

The physical activity/posture sensor 416 may include an implantable, wearable, holdable, or otherwise ambulatory sensor for sensing an intensity of physical activity or a posture state of the subject. The physical activity/posture sensor may include a single-axis or a multi-axis accelerometer configured to sense an acceleration signal of at least a portion of the subject's body. The strength of the acceleration signal can be indicative of the physical activity level. In another example, the activity sensor can include a respiratory sensor configured to measure respiratory parameters correlative or indicative of respiratory exchange, i.e., oxygen uptake and carbon dioxide output. In an example, posture can be represented by, for example, a tilt angle sensed by a tilt switch. In another example, patient posture or physical activity information can be derived from thoracic impedance information. In healthy subjects, physical activity and posture may each follow a circadian rhythm. For instance, physical activity intensity is typically higher during the day and reduces at night, and a standing or upright posture usually occurs during the day and a lying posture occurs at night. This circadian rhythm of physical activity or posture, however, may become less pronounced or otherwise change several hours to several days before the onset of a disease state, such as a worsening heart failure. Monitoring the circadian rhythm of physical activity or posture in such instances provides a tool to predict, monitor, or treat an occurrence of impending heart failure.

The chemical sensor 417 may include an implantable, wearable, holdable, or otherwise ambulatory sensor for sensing level or change of blood chemistry. By way of non-limiting example, the chemical sensor 417 may sense blood electrolyte level such as one or more of potassium (K), sodium (Na) calcium (Ca), glucose, or creatinine. In an example, the chemical sensor 417 may sense a level, or a change of, blood pH. An example of an approach to providing a chemical sensor is disclosed in the commonly assigned Kane et al., U.S. Pat. No. 7,809,441, entitled "IMPLANTABLE MEDICAL DEVICE WITH CHEMICAL SENSOR AND RELATED METHODS," filed May 17, 2006, which is hereby incorporated by reference in its entirety, including its disclosure of implantable sensors and sensing methods associated with changes in the blood electrolytes or pH in healthy subjects, blood chemistry such as levels of one or more electrolytes may follow a circadian rhythm. This circadian rhythm may be less pronounced or otherwise change prior to an onset of a disease state, such as a worsening heart failure. Monitoring the circadian rhythm of the blood chemistry in such instances provides a tool to predict, monitor, or treat an occurrence of impending heart failure.

The CRI generator 420, which may be an embodiment of the CRI generator 224, may receive the sensor signals sensed by various sensors in the sensor circuit 410, and generate respective CRIs from the sensor signals. The reference CRI generator 260 may generate, for the various sensor signals, respective rCRI associated with a prior hospital admission event. In an example, as previously discussed with reference to FIG. 3, the rCRI may be generated during a specified time period such as a pre-admission period, a post-discharge period, or a delayed post-discharge period associated with prior hospital admission.

The readmission risk generator 430, which may be an embodiment of the readmission risk generator 232, may include a comparator circuit 432 to compare the CRIs with the corresponding rCRIs, and a fusion circuit 434 to determine a readmission risk using a combination of the comparisons between the CRIs and the corresponding rCRIs. In an example, the comparator circuit 432 may compute pair-wise difference or other similarly measure between the CRI and the corresponding rCRI for each of the sensor signals or of a subset of the sensor signals such as selected by the sensor selector circuit 222, and the fusion circuit 434 may determine the readmission risk score (R) as weighted combination, or other linear or nonlinear combination, of the pair-wise differences for all or the selected subset of the sensor signals, such as according to Equation (1) below:

$$R = \Sigma w(i) \cdot [CRI(i) - rCRI(i)] \quad (1)$$

where w(i) is a weight factor for sensor signal $X_i$. In another example, the readmission risk generator 430 may compute a composite CRI as a weighted combination of the CRIs for all or a selected subset of the sensor signals, and compute a composite rCRI as a weighted combination of the rCRIs for all or a selected subset of the sensor signals. The readmission risk may be determined as a difference, ratio, or similarly measure between the composite CRI and the composite rCRI, such as according to Equation (2) below:

$$R = \Sigma u(i) \cdot CRI(i) - \Sigma v(j) \cdot rCRI(j) \quad (2)$$

where u(i) is a weight factor for CRI(i) and v(j) is a weight factor for rCRI(j).

In some examples, the readmission risk generator 430 may determine the readmission risk score using time elapsed ($\Delta T$) from the prior hospital admission event. A more recent hospital admission event (corresponding to a smaller $\Delta T$) may put the patient at a higher readmission risk than a more remote hospital admission in the past (corresponding to a larger $\Delta T$). In an example, the weight factors, such as the weight factors w, u or v in Equations (1) and (2) for computing the readmission risk R, may be determined based on the elapsed time $\Delta T$. In an example, the rCRIs are computed using signals or signal metric trends in a post-discharge period. The weight factors w, u or v may be inversely proportional to the elapsed time $\Delta T$. This may be useful when different sensor signals are measured at different time. For example, if CRI(i) is measured from sensor signal X(i) at a time closer to the prior hospital admission event (i.e., a smaller $\Delta T$), while CRI(j) is measured from sensor signal X(j) at a time more distant away from the prior hospital admission event (i.e., a larger $\Delta T$), then in Equation (1), the weight w(i) for difference [CRI(i)–rCRI(i)] would be larger than the weight factor w(j) for the difference [CRI(j)–rCRI(j)].

Figure 5A:
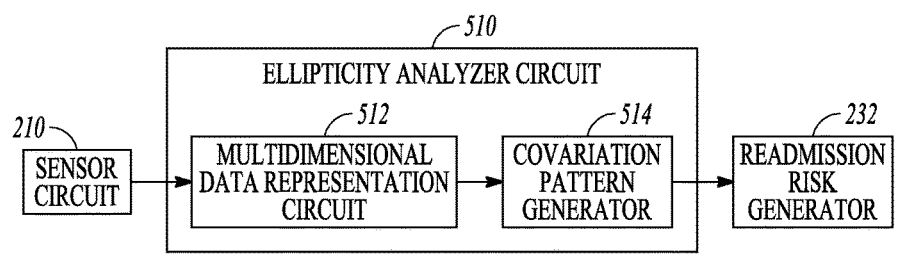
FIGS. 5A-B illustrate generally examples of an ellipticity analyzer circuit for determining a chronobiological rhythm indicator using a plurality of physiological signals or signal metric trends.
Figure 5B:
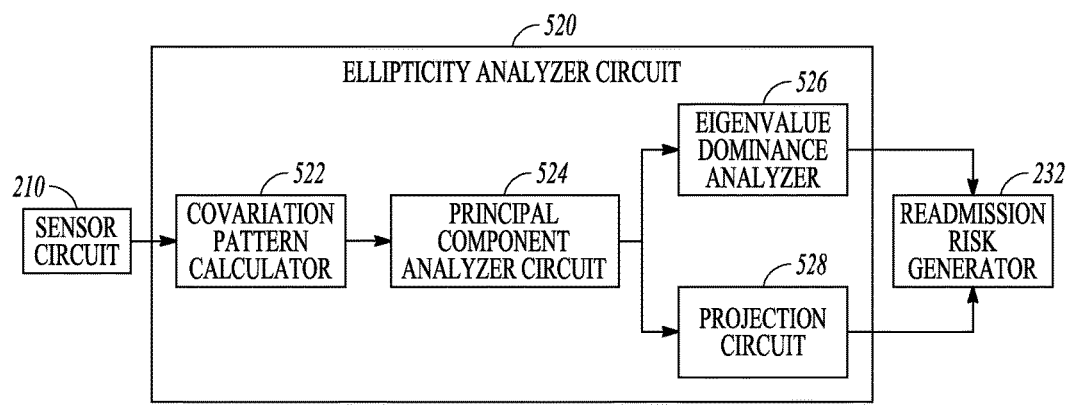

FIGS. 5A-B illustrate generally examples of an ellipticity analyzer circuit for determining a chronobiological rhythm indicator using a plurality of physiological signals or signal metric trends. The ellipticity analyzer circuit 510 in FIG. 5A and the ellipticity analyzer circuit 520 in FIG. 5B may each be an embodiment of the CRI generator 224 for generating the CRI from a physiological signal or signal metric trend, or an embodiment of the reference CRI generator 260 for generating the rCRI associated with a prior hospital admission event.

As illustrated in FIG. 5A, the ellipticity analyzer circuit 510 may include a multidimensional signal representation circuit 512 for receiving two or more physiological signals or signal metric trends from the sensor circuit 210, and representing the signals or signal metric trends in a multidimensional signal space. In an example, the multidimensional signal space may be spanned by a heart rate in a first axis, a HS metric such as S1 intensity in a second axis, and a thoracic impedance magnitude in a third axis. Multiple measurements of heart rate, S1 intensity and thoracic impedance magnitude may be represented as a cloud of data points in the multidimensional signal space, where each data point represents the heart rate, the S1 intensity, and the thoracic impedance magnitude measured substantially simultaneously, such as during the same cardiac cycle or within the same data acquisition window.

The covariation pattern generator 514 may determine an ellipticity attribute from the multidimensional data representation. In an example, the covariation pattern generator 514 may generate a multidimensional ellipse based on the statistical distribution of the multidimensional data. The multidimensional ellipse is a graphical representation of the covariation pattern among multiple signal metrics. If multiple signal metrics strongly covariate with one another, then there is a high likelihood of an underlying chronobiological rhythm such that different sensor signals or signal metrics represent similar physiology. The multidimensional data representation with strong covariation may graphically manifest in the multidimensional signal space more of an ellipse than a circle. If multiple signal metrics weakly covariate with one another, then there is a low likelihood of an underlying chronobiological rhythm. The multiple signal metrics may represent dissimilar physiology. The multidimensional data representation with weak covariation may graphically manifest in the multidimensional signal space less of an ellipse, but more of a circle.

The readmission risk generator 232 may compare the CRI represented as the covariation pattern (CP) among multiple signals or signal metrics to the rCRI represented as the reference covariation pattern (rCP) among multiple signals or signal metrics associated with a prior hospital admission event. The readmission risk generator 232 may determine the readmission risk using a similarity measure between CP and rCP. Examples of the similarity measure may include Euclidian distance, correlation coefficient, or mutual information, among others. In an example, the rCP is determined using signals or signal metrics during a post-discharge period when the patient is recovered from hospitalization for a chronic disease. The rCP may have a graphical pattern more of an ellipse. If the CP has a graphical pattern of an ellipse and is substantially similar to rCP (such as if the similarity measure exceeds a threshold), then a high chronobiological rhythm is indicated, and a low readmission score may be generated. If the CP has a graphical pattern more of a circle than an ellipse, such as that it is substantially dissimilar to rCP (such as if the similarity measure falls below a threshold), then it indicates the chronobiological rhythm has been lost or substantially diminished, and the patient's chronic disease state deteriorates and a high readmission risk score may be determined.

As illustrated in FIG. 5B, the ellipticity analyzer circuit 520 may include the multidimensional data representation circuit 512 a covariance matrix calculator 522, a principal component analyzer circuit 524, and one or both of an eigenvalue dominance analyzer 526 and a projection circuit 528. The covariance matrix calculator 522 may receive two or more physiological signals or signal metrics and compute a covariance matrix. For N signals or signal metrics, the covariance matrix would be an N-by-N matrix. The principal component analyzer circuit 524 performs principal component analysis (PCA), such as by using a Karhunen Loeve Transform (KLT), on the covariance matrix. The PCA analysis may result in a plurality of principal components and corresponding eigenvalues for the principal components. The principal components are orthogonal dimensions or uncorrelated directions in the multidimensional signal space, and can be viewed as a subset of all possible eigenvectors. For a N-by-N covariance matrix, up to N principal components (e.g., $V_1, V_2, \ldots V_N$) and corresponding N eigenvalues (e.g., $\lambda_1, \lambda_2, \ldots$) can be obtained. In some examples, the principal components may be sorted (e.g., in descending order) according to the variance of the projections of the multidimensional data along the principal components. The first principal component may have as high a variance as possible. Each succeeding principal component has the next highest variance possible and is constrained to be orthogonal to the preceding principal components.

In an example where two signals or signal metrics, X and Y, are involved, the ellipticity analyzer circuit 520 may generate a 2-by-2 matrix:

$$Cxy = \begin{bmatrix} \sigma_x^2 & \rho_{xy} \\ \rho_{xy} & \sigma_y^2 \end{bmatrix}$$

where $\sigma_x^2$ is the variance of the first signal X, $\sigma_y^2$ is the variance of the second signal Y, and $\rho_{xy}$ is the covariation between the signals X and Y. By applying the KLT, the covariance matrix Cxy may be transformed into a diagonal matrix of eigenvalues $\lambda_1$ and $\lambda_2$:

$$Cxy' = \begin{bmatrix} \lambda_1 & 0 \\ 0 & \lambda_2 \end{bmatrix}$$

By way of example and not by limitation, the eigenvalue dominance analyzer 526 and the projection circuit 528 provide two approaches for assessing readmission risk, either or both of which may be included in the ellipticity analyzer circuit 520. The eigenvalue dominance analyzer 526 may determine a relative measure among the plurality of eigenvalues. The relative measure may indicate dominance of the maximum eigenvalue ($\lambda_{max}$) among all the eigenvalues. A more dominant $\lambda_{max}$ may indicate a higher ellipticity of the multidimensional data representation in the multidimensional signal space, or a graphical pattern more of an ellipse than a circle. Conversely, a less dominant $\lambda_{max}$ may indicate a lower ellipticity of the multidimensional data representation, or a graphical pattern more of a circle than an ellipse. In an example, the relative measure may be calculated using a ratio of $\lambda_{max}$ to a sum of all the eigenvalues $\Sigma\lambda_i$, as provided in Equation (3) below:

$$L = \frac{\lambda_{max}}{\Sigma \lambda_i} \quad (3)$$

Alternatively, the ellipticity L may be determined based on a statistical distribution of the eigenvalues, such as a range, spreadness, skewness, variance of the eigenvalues. In an example, the ellipticity may be determined as a difference between $\lambda_{max}$ and the minimum eigenvalue $\lambda_{min}$. A greater difference ($\lambda_{max}-\lambda_{min}$) may indicate greater dominance of $\lambda_{max}$ and thus higher ellipticity. In another example, the ellipticity may be determined as a different, or a ratio, between $\lambda_{max}$ and a mean, median, mode or other central tendency measure of all the eigenvalues. A greater ratio of $\lambda_{max}$ and the central tendency of eigenvalues, or a greater difference between $\lambda_{max}$ and the central tendency of eigenvalues, may indicate greater dominance of $\lambda_{max}$ and thus higher ellipticity.

The readmission risk generator 232 may determine the readmission risk based on a relative change of the ellipticity (L) such as given in Equation (3) above from the reference ellipticity (rL) associated with a prior hospital admission event. In an example, the rL may be determined using two or more signals or signal metrics acquired during a post-discharge period when the patient is recovered from hospitalization for a chronic disease. If the ellipticity L is greater than or substantially equal to the reference ellipticity attribute rL, then a high chronobiological rhythm is indicated, and a low readmission score may be generated. However, if the ellipticity L falls below the reference ellipticity attribute rL by a specified margin, then it indicates the chronobiological rhythm has been lost or substantially diminished, the chronic disease state has deteriorated, and a high readmission risk score may be generated.

The projection circuit 528 may generate a projection of the multidimensional data received from the sensor circuit 210 along at least one of the principal components. The projection is a transform that reduces the dimension of the multidimensional data to a dimension determined by the principal components. The multidimensional data may be represented by a data matrix, and each principal component represented as a vector. The projection may involve matrix-matrix multiplication or matrix-vector multiplication. In an example, the projection circuit 528 may project the multidimensional data along one principal component such as corresponding to $\lambda_{max}$, resulting in one-dimensional transformed data. In another example, the projection circuit 528 may project the multidimensional data along two principal components such as corresponding the maximal and second maximal eigenvalues, resulting in a two-dimensional transformed data.

In an example, the ellipticity analyzer circuit 520 may be an embodiment of the reference CRI generator 260, and configured to generate ellipticity attributes associated with a prior hospital admission event. The covariance matrix calculator may compute a reference covariance matrix using a plurality of physiological signals or signal metric trends during respective time periods (such as a pre-admission period or a post-discharge period) associated with the prior hospital admission event. The principal component analyzer circuit 524 may determine two or more reference principal components from the reference covariance matrix. At least one of the reference principal components may be used for data transformation. The projection circuit 528 may determine a first projection of the multidimensional data along at least one of the reference principal components. The first projection represents transformed data from which a readmission risk is to be assessed. The projection circuit 528 may determine a second projection of a multidimensional data associated with the prior hospital admission event along the at least one of the reference principal components. The second projection represents transformed data associated with prior hospital admission. A CRI may be generated from first projection, and a reference CRI (rCRI) may be generated from the second projection. The CRI (or rCRI) may be calculated as a statistical measure of daily (or other periodic) maximum-to-minimum intensity difference of a respective projection, or a spectral parameter obtained from the spectral analysis of the respective projection. The readmission risk generator 232 may determine the readmission risk score including a relative change from rCRI to CRI.

Figure 6:
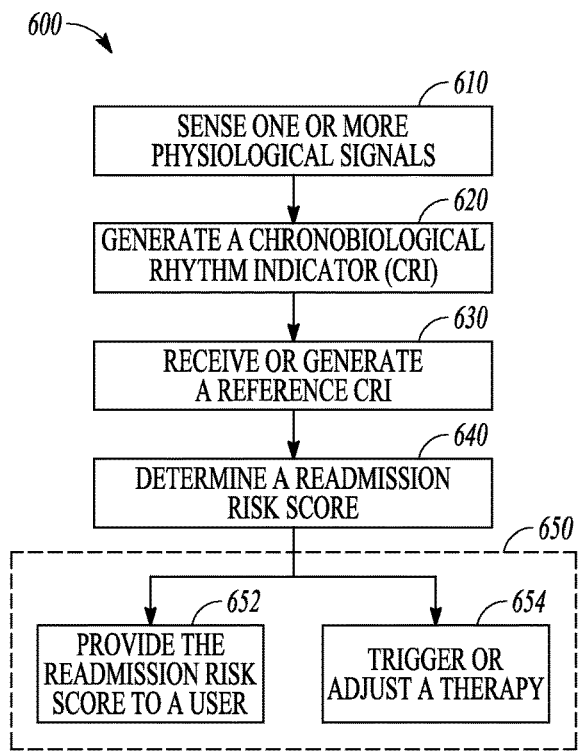
FIG. 6 illustrates generally an example of a method for monitoring a chronic disease in a patient to determine a risk of hospital readmission.

FIG. 6 illustrates generally an example of a method 600 for monitoring a chronic disease in a patient, such as a chronic heart disease such as heart failure or coronary artery disease, a chronic pulmonary disease such as asthma, bronchoconstriction, COPD, or pulmonary fibrosis, pneumoconiosis, or a chronic kidney disease, among others. The method 600 may be used to monitor the patient's chronic disease state following patient's discharge from the hospital, and to determine a risk of hospital readmission for worsening of chronic disease. The method 600 may be implemented and operate in an ambulatory medical device such as an implantable, wearable, or holdable medical device, or in a remote patient management system. In an example, the method 500 may be executed by the readmission risk analyzer module 160 or by the external system 125. In an example, the method 600 may be implemented in, and executed by, the chronic disease monitoring system 200 or any embodiments thereof.

The method 600 begins at 610 by sensing one or more physiological signals such as via implantable, wearable, holdable, or otherwise ambulatory sensors, which may include, by way of example and not limitation, pressure sensors, flow sensors, impedance sensors, accelerometers, microphone sensors, respiration sensors, temperature sensors, or chemical sensors, among others. Examples of the physiological signals sensed by the physiological sensor circuit 210 may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, a blood chemistry signal such as a blood electrolyte level signal, glucose level signal or creatinine level signal, central venous pH value, a heart sound (HS) signal, an endocardial acceleration signal, an angular momentum signal, a posture signal, a physical activity signal, or a respiration signal, among others. One or more signal metrics may be generated from the sensed physiological signals, and trended over time to form respective signal metric trends.

At 620 a chronobiological rhythm indicator (CRI) may be generated from the sensed physiological signals. The CRI may be determined using multiple measurements of daily (or other periodic) maximum-to-minimum intensity difference of signal X (denoted by $X_{pp}$) over a specified time period, such as approximately 5-10 days. Alternatively, the CRI may include one or more spectral parameters obtained from a spectral analysis of the selected physiological signals or signal metric trends, such as power of a spectral peak corresponding to the circadian rhythm, a center frequency of the spectral peak, or a bandwidth of the spectral peak. In some examples, the CRI may be an ellipticity attribute represented in a multidimensional signal space spanned by two or more selected physiological signals or signal metrics, as to be discussed below with reference to FIG. 7.

At 630, a reference CRI (rCRI) may be provided by a system user, or generated from physiological signals or signal metric trends over a specified time period such as associated with prior hospital admission. In an example, the rCRI may be determined from physiological signals or signal metric trends during a post-discharge period of approximately 2-5 days following the prior hospital admission event. In another example, the rCRI may be determined from physiological signals or signal metric trends during a delayed post-discharge period that does not begin until after a post-discharge transition when the patient's health status is improved and stabilized. In an example, the rCRI may be determined from physiological signals or signal metric trends during a pre-admission period of approximately 2-5 days preceding the prior hospital admission event.

At 640, a readmission risk score may be generated using the CRI and the rCRI. The readmission risk score may indicate a degree of risk of subsequent hospital readmission due to a worsened condition of the chronic disease. The readmission risk score may be determined as a difference, ratio, or other relative measure between CRI and rCRI, or a similarity measure between an ellipticity attribute and a reference ellipticity attribute based on ellipticity analysis of multidimensional data of the physiological signals or signal metrics, as to be discussed below with reference to FIG. 7. The readmission risk score may take continuous values. The readmission risk score may be compared to one or more threshold values or ranges, and categorized into discrete categorical levels such as high, medium, or low risk of readmission.

In an example, the readmission risk score may be calculated using a relative change of CRI from a post-discharge rCRI or a delayed post-discharge rCRI. The post-discharge rCRI or the delayed post-discharge rCRI may represent a chronobiological rhythm indicating improved health status. If the difference between CRI and post-discharge rCRI or delayed post-discharge rCRI falls below a threshold value, then a strong chronobiological rhythms is indicated, and a low readmission risk score is generated. In another example, the readmission risk score may be calculated using a relative change of CRI from a pre-admission rCRI. The pre-admission rCRI may correspond to worsened chronic disease state prior to hospital admission. If the difference between the CRI and the pre-admission rCRI exceeds a threshold value, then a strong chronobiological rhythm is indicated, and a low readmission risk score is generated. In an example, the readmission risk score may be determined using a weighted combination of a difference between CRI and the pre-admission rCRI and a difference between the CRI and the post-discharge CRI or the delayed post-discharge rCRI.

In various examples, the CRI at 620 may be generated from a subset of the plurality of candidate physiological signals or signal metrics selected based on the physiological signal or signal metric's sensitivity to patient chronobiological rhythms. Generally, a signal or signal metric that manifests a higher level of daily, weekly, monthly, or seasonal oscillatory pattern may be more sensitive to chronobiological rhythms than a signal or signal metric showing no or lower level of chronological oscillatory pattern, and may thus be selected for generating the CRI. In an example, the subset of physiological signals or signal metrics may be selected based on the reference CRIs (rCRIs) associated with a particular time period of the prior hospital admission. For example, a signal metric having a larger post-discharge rCRI or a smaller pre-admission rCRI, has a higher sensitivity to a post-discharge recovery of chronobiological rhythm, and may therefore be preferred over a signal metric having a smaller post-discharge rCRI or a larger pre-admission rCRI. In another example, a signal or signal metric having a larger change from pre-admission to post-discharge rCRI value is more sensitive to a recovery process of chronobiological rhythm from pre-admission to post-discharge recovery period, and may therefore be selected for use in readmission risk estimation.

In some examples, the readmission risk score may be determined using chronobiological rhythm indicators (CRIs) generated from multiple physiological signals or signal metrics. Examples of the physiological signals may include heart rate signal, heart rate variability signal, heart sound signal, endocardial acceleration signal, angular momentum signal, thoracic impedance signal, respiration signal, pressure signal such as cardiovascular blood pressure signal or thoracic pressure signal, physical activity intensity signal, or posture signal. Circadian rhythms (or oscillatory patterns at other periods) of one or more of these physiological signals, when lost, diminished, or otherwise changed from a reference level such as at a time period during a prior hospital admission, may be associated with a change of chronic disease status. CRIs for the multiple signals or signal metrics may be generated at 620, and the corresponding rCRIs for the multiple signals or signal metrics may be generated at 630. A readmission risk score may be generated at 640, such as via the fusion circuit 434, using a weighted combination of the difference, ratio, or similarly measure between the CRI and the corresponding rCRI for all or a selected subset of the physiological signals.

At 650, the readmission risk score may be provided to a user or a process. At 552, a human-perceptible presentation of the readmission risk score, or the CRI and the rCRI, may be generated, and displayed such as on the user interface 250. The information may be presented in a table, a chart, a diagram, or any other types of textual, tabular, or graphical presentation formats. An alert may be generated in response to the respiratory restriction/obstruction indicator satisfying a specified condition, such as exceeding an alert threshold. Additionally or alternately, at 654, the readmission risk score may be used to trigger or adjust a therapy delivered to the patient. Examples of the therapy may include electro-stimulation therapy delivered to the heart, a nerve tissue, other target tissues in response to the detection of the target physiological event, or drug therapy including delivering drug to a tissue or organ. In some examples, the detection or the classification of the restrictive or obstructive respiratory condition may be used to modify an existing therapy, such as to adjust a stimulation parameter or drug dosage.

Figure 7:
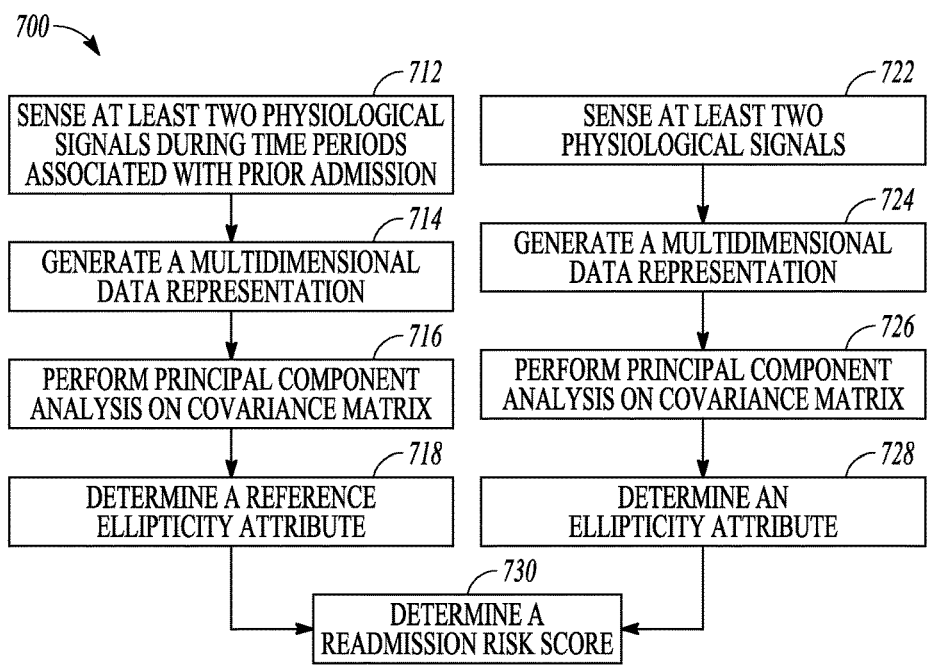
FIG. 7 illustrates generally an example of a method for determining a chronobiological rhythm indicator based on ellipticity analysis of a plurality of physiological signals or signal metric trends.

FIG. 7 illustrates generally an example of a method 700 for determining a chronobiological rhythm indicator based on ellipticity analysis of at least two physiological signals or signal metric trends. The method 700 may be executed by the ellipticity analyzer circuits 510 or 520 as illustrated in FIGS. 5A-B, or any embodiments thereof.

The method 700 may include steps 712-718 for determining a reference ellipticity attribute, and steps 722-728 for determining an ellipticity attribute. At 712, at least two physiological signals or signal metric may be sensed during a time period associated with a specified event in the patient's medical history, such as a pre-admission period or a post-discharge period associated with a prior hospital admission event. At 714, a multidimensional data representation of the two or more signals or signal metrics may be generated in a multidimensional signal space. Each dimension (or axis) of the multidimensional signal space may be represented by a physiological signal or signal metric. For example, the multidimensional signal space may be spanned by a heart rate in a first axis, a S1 heart sound intensity in a second axis, and a thoracic impedance magnitude in a third axis. A multidimensional data representation may be represent as a cloud of data points in the multidimensional signal space, including multiple measurements of the heart rate, the S1 intensity, and the thoracic impedance magnitude during the prior hospital admission event.

At 716, a covariance matrix may be generated using the multidimensional data representation, and a principal component analysis (PCA) may be performed on the covariance matrix. As previously discussed with reference to FIG. 5B, the PCA may include a Karhunen Loeve Transform (KLT) of the covariance matrix that produces a plurality of reference principal components and corresponding reference eigenvalues for the reference principal components. The reference principal components are orthogonal dimensions or uncorrelated directions in the multidimensional signal space.

At 718, a reference ellipticity attribute may be determined using the eigenvalues or the principal components. In an example, the reference ellipticity attribute (rL) may include a measure of dominance of the maximum reference eigenvalue ($\lambda_{max}$) among all the reference eigenvalues, such as determined according to Equation (3). A more dominant $\lambda_{max}$ may indicate a higher ellipticity of the multidimensional data representation in the multidimensional signal space, or a graphical pattern more of ellipse than circle. Conversely, a less dominant $\lambda_{max}$ may indicate a lower ellipticity of the multidimensional data representation, or a graphical pattern more of circle than ellipse. In another example, the reference ellipticity attribute (rL) may include a projection of the multidimensional data, as generated at 714, along one or more reference principal components. The projection may be performed using matrix-matrix multiplication or matrix-vector multiplication, where the multidimensional data is represented by a matrix and each reference principal component may be represented as a vector. The projection represents transformed data associated with the prior hospital admission event.

Similar to steps 712-718, an ellipticity attribute may be generated from at least two physiological signals or signal metrics. In contrast to 712 where the signals or signal trends are sensed during a time period associated with prior hospital admission, at 722 the signals or signal trends may be sensed during a time period subsequent to the prior hospital admission and an assessment of patient's risk of readmission is needed. A multidimensional data representation of the two or more physiological signals or signal metric trends may be generated at 724, and at 726 PCA may be performed on a covariance matrix generated from the multidimensional data representation. An ellipticity attribute may be generated at 728, which may include a dominance measure of the maximum eigenvalue $\lambda_{max}$ among all the eigenvalues obtained from PCA of the covariance matrix, such as determined according to Equation (3).

In an example, the ellipticity attribute at 728 may include a projection of the multidimensional data, as generated at 724, along one or more reference principal components generated at 716 through PCA of the covariance matrix of the multidimensional data associated with the prior hospital admission event. If the ellipticity attribute is represented only by the projection onto one or more reference principal components, the step 726 may be omitted. The projection represents transformed data from which the patient's readmission risk is to be assessed.

At 730, a readmission risk score may be generated using the reference ellipticity attribute and the ellipticity attribute. In an example, the reference ellipticity attribute includes a dominance of the maximum reference eigenvalue, which is computed from signals acquired during a post-discharge period when the patient is recovered from hospitalization for a chronic disease. The ellipticity attribute includes a dominance of the maximum eigenvalue. If the ellipticity (L) is greater than or substantially equal to the reference ellipticity attribute (rL), then a high chronobiological rhythm is indicated, and a low readmission score may be generated. However, if the ellipticity L falls below the reference ellipticity attribute rL by a specified margin, then it indicates the chronobiological rhythm has lost or substantially diminished, and the patient's chronic disease state deteriorates and a high readmission risk score is determined.

In another example, the readmission risk score may be determined at 730 using a first projection of the multidimensional data generated at 724 along one or more reference principal components, and a second projection of the multidimensional data generated at 714 along the same one or more reference principal components. A CRI may be generated from first projection, such as a statistical measure of daily (or other periodic) maximum-to-minimum intensity difference of the first projection, or spectral parameters obtained from the spectral analysis of the first projection. A reference CRI (rCRI) may be generated from the second projection, such as a statistical measure of daily (or other periodic) maximum-to-minimum intensity difference of the second projection, or spectral parameters obtained from the spectral analysis of the second projection. The readmission risk generator may then be calculated using a relative change of the CRI from the rCRI.

In some examples, the ellipticity attribute at 718 may include a reference covariance pattern (rCP) generated from the multidimensional data representation at 714, and the ellipticity attribute at 728 may include a covariance pattern (CP) generated from the multidimensional data representation at 724. The rCP and CP may each have a graphical representation in the multidimensional signal space. The multidimensional data representation with strong covariation among signal metrics may have a graphical pattern more of an ellipse than a circle, while the multidimensional data representation with weak covariation may have a graphical pattern more of a circle than an ellipse. At 730, the readmission risk score may be determined based on a similarity measure between the rCP and CP. Examples of the similarity measure may include Euclidian distance, correlation coefficient, or mutual information, among others. If the similarity measure exceeds a threshold, then a high chronobiological rhythm is indicated, and a low readmission score may be generated. If the similarity measure falls below a threshold, then it indicates the chronobiological rhythm has been lost or substantially diminished, and the patient's chronic disease state deteriorates and a high readmission risk score may be determined.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for managing a patient with a chronic disease, comprising:
   a sensor circuit including sense amplifier circuits to sense one or more physiological signals;
   a signal processor circuit configured to generate a chronobiological rhythm indicator (CRI) from the one or more physiological signals; and
   a detector circuit coupled to the signal processor circuit and configured to determine a readmission risk score using the generated CRI and a reference CRI associated with a prior hospital admission event of the patient, the readmission risk score indicating a degree of risk of subsequent hospital readmission for a worsened condition of the chronic disease; and
   an output circuit configured to provide the readmission risk score to a user or a process.

2. The system of claim 1, comprising a therapy circuit adapted to initiate or adjust a therapy delivered to the patient in response to the readmission risk score satisfying a condition.

3. The system of claim 1, wherein the chronic disease includes a heart failure, and the signal processor circuit is configured to generate the CRI from the one or more physiological signals including:
   a heart sound signal;
   a heart rate signal;
   a thoracic impedance signal;
   a respiration signal;
   a pressure signal;
   a chemical signal;
   an activity intensity signal; or
   a posture signal.

4. The system of claim 1, further comprising a sensor selector circuit configured to select at least one physiological signal from the two or more physiological signals according to the reference CRI associated with the prior hospital admission event; and
   wherein the detector circuit is configured to determine the readmission risk score using the generated CRI generated from the selected at least one physiological signal.

5. The system of claim 1, wherein:
   the signal processor circuit is configured to generate one or more reference CRIs from one or more physiological signals sensed during one or more time periods including a post-discharge period following the prior hospital admission event or a pre-admission period preceding the prior hospital admission event; and
   the detector circuit is configured to determine the readmission risk score using a comparison between the generated CRI and the one or more reference CRIs during the post-discharge period or the pre-admission period.

6. The system of claim 1, wherein:
   the processor circuit is configured to generate a first CRI from a first physiological signal and a second CRI from a different second physiological signal; and
   the detector circuit is configured to:
      generate a first reference CRI from the first physiological signal during a first time period associated with the prior hospital admission event, and a second reference CRI from the second physiological signal during a second time period associated with the prior hospital admission event; and
      determine the readmission risk score using both a comparison between the first CRI and the first reference CRI and a comparison between the second CRI and the second reference CRI.

7. The system of claim 1, wherein detector circuit is configured to determine a readmission risk score further using time elapsed from the prior hospital admission event.

8. The system of claim 1, wherein:
   the sensor circuit is configured to sense at least two physiological signals; and
   the signal processor circuit includes an ellipticity analyzer circuit configured to form a multidimensional data representation of the at least two physiological signals in a multidimensional signal space, and determine an ellipticity attribute from the multidimensional data representation; and
   the signal processor circuit is configured to generate the CRI using the ellipticity attribute.

9. The system of claim 8, wherein:
   the signal processor circuit is configured to generate the reference CRI including a reference ellipticity attribute from a multidimensional data representation of at least two physiological signals during respective time periods associated with the prior hospital admission event; and
   the detector circuit is configured to determine the readmission risk score including a relative change of the ellipticity attribute from the reference ellipticity attribute.

10. The system of claim 8, wherein the ellipticity analyzer circuit is configured to determine the ellipticity attribute including a covariation pattern of the at least two physiological signals in the multidimensional signal space.

11. The system of claim 8, wherein the ellipticity analyzer circuit is configured to:
   compute a covariance matrix using the at least two physiological signals;
   determine, from the covariance matrix, two or more principal components in the multidimensional signal space or a plurality of eigenvalues associated with the two or more principal components; and
   determine the ellipticity attribute using the two or more principal components, a projection of the multidimensional data representation along at least one of the two or more determined principal components, or a relative measure among the plurality of eigenvalues.

12. The system of claim 11, wherein the ellipticity analyzer circuit is configured to:
   compute a reference covariance matrix using the at least two physiological signals during respective time periods associated with the prior hospital admission event; and
   determine two or more reference principal components from the reference covariance matrix;
   determine a first projection of the multidimensional data representation along at least one of the reference principal components, and a second projection of a multidimensional data representation of the at least two physiological signals associated with the prior hospital admission event along the at least one of the reference principal components; and
   generate the CRI from first projection and generate the reference CRI from the second projection; and
   wherein the detector circuit is configured to determine the readmission risk score including a relative change of the CRI from the reference CRI.

13. A method for managing a patient with a chronic disease, comprising:
- sensing one or more physiological signals;
- generating a chronobiological rhythm indicator (CRI) from the one or more physiological signals; and
- receiving a reference CRI associated with a prior hospital admission event of the patient; and
- determining a readmission risk score using the generated CRI and the reference CRI, the readmission risk score indicating a degree of risk of subsequent hospital readmission for a worsened condition of the chronic disease; and
- providing the readmission risk score to a user or a process.

14. The method of claim 13, further comprising adjusting or initiating a therapy, via a therapy delivery circuit, for delivery to the patient in response to the readmission risk score satisfying a condition.

15. The method of claim 13, further comprising selecting at least one physiological signal from the two or more physiological signals according to the reference CRI associated with the prior hospital admission event; and
- wherein the readmission risk score is determined using the CRI generated from the selected at least one physiological signal.

16. The method of claim 13, comprising generating one or more reference CRIs from one or more physiological signals sensed during time periods including a post-discharge period following the prior hospital admission event or a pre-admission period preceding the prior hospital admission event; and
- wherein the readmission risk score is determined using a comparison between the generated CRI and the one or more reference CRIs during the post-discharge period or the pre-admission period.

17. The method of claim 13, wherein:
- generating the CRI includes generating a first CRI from a first physiological signal and a second CRI from a different second physiological signal; and
- receiving the reference CRI includes generating a first reference CRI from the first physiological signal during a first time period associated with the prior hospital admission event, and a second reference CRI from the second physiological signal during a second time period associated with the prior hospital admission event; and
- determining the readmission risk score includes a combination of both a comparison between the first CRI and the first reference CRI and a comparison between the second CRI and the second reference CRI.

18. The method of claim 13, wherein:
- generating the CRI includes generating a multidimensional data representation of at least two physiological signals in a multidimensional signal space, and determining an ellipticity attribute from the multidimensional data representation;
- receiving the reference CRI includes generating a reference ellipticity attribute from a multidimensional data representation of at least two physiological signals during respective time periods associated with the prior hospital admission event; and
- determining the readmission risk score including computing a relative change of the ellipticity attribute from the reference ellipticity attribute.

19. The method of claim 18, wherein the ellipticity attribute includes a covariation pattern of the intensities of the at least two physiological signals in the multidimensional signal space.

20. The method of claim 18, wherein determining the ellipticity attribute includes:
- computing a covariance matrix using the at least two physiological signals;
- determining, from the covariance matrix, two or more principal components or a plurality of eigenvalues associated with the two or more principal components; and
- determining the ellipticity attribute using the two or more principal components, a projection of the multidimensional data representation along at least one of the two or more determined principal components, or a relative measure among the plurality of eigenvalues.

* * * * *